(12) United States Patent
Hayashi et al.

(10) Patent No.: US 6,342,603 B1
(45) Date of Patent: Jan. 29, 2002

(54) PURINE DERIVATIVES HAVING CYCLOPROPANE RING

(75) Inventors: Taketo Hayashi; Junichi Yasuoka; Akito Nishiura, all of Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 09/541,724

(22) Filed: Apr. 3, 2000

Related U.S. Application Data

(62) Division of application No. 09/184,747, filed on Nov. 3, 1998, now Pat. No. 6,156,892.

(30) Foreign Application Priority Data

| Nov. 12, 1997 | (JP) | ............................................. | 9-310839 |
| May 15, 1998 | (JP) | ........................................... | 10-133349 |
| Jun. 29, 1998 | (JP) | ........................................... | 10-182765 |

(51) Int. Cl.[7] .................... C07D 473/40; C07D 473/18; C07D 473/32; C07D 473/28; C07D 473/30

(52) U.S. Cl. ...................... 544/264; 544/265; 544/276; 544/277

(58) Field of Search ................................ 544/264, 265, 544/276, 277

(56) References Cited

U.S. PATENT DOCUMENTS

| 3,495,012 A | 2/1970 | Minieri et al. | ............... | 424/313 |
| 4,988,703 A | 1/1991 | Norbeck et al. | ............ | 514/262 |

FOREIGN PATENT DOCUMENTS

| EP | 0 182024 A2 | 5/1986 |
| EP | 0 302644 A2 | 2/1989 |
| EP | 0 369583 A1 | 5/1990 |
| EP | 0 420559 A2 | 4/1991 |
| JP | 3120279 A | 5/1991 |
| JP | 586792 B2 | 12/1993 |

OTHER PUBLICATIONS

Geen et al., *Bioorganic & Medicinal Chemistry Letters*, vol. 1, No. 7, pp. 347–348 (1991).
Choudary et al., *Nucleosides & Nucleotides*, vol. 15, No. 5, pp. 981–994 (1996).
Izawa, J. Chem Soc, Perkins 1, p. 2519 (1992).
Kato, Chem Abs 118:255264m (Oct. 1992).

*Primary Examiner*—Mark L. Berch
(74) *Attorney, Agent, or Firm*—Birch, Stewart, Kolasch & Birch, LLP

(57) ABSTRACT

The present invention is directed to a process for preparing a cyclopropane ring-cleaved purine derivative represented by the following formula:

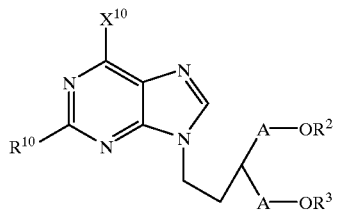

comprising hydrogenating a purine derivative having a cyclopropane ring represented by the following formula:

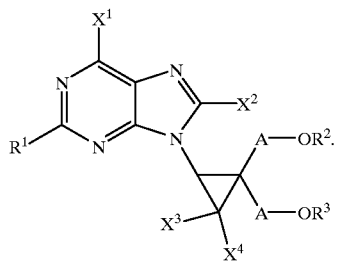

1 Claim, No Drawings

PURINE DERIVATIVES HAVING CYCLOPROPANE RING

This application is a divisional of application Ser. No. 09/184,747, filed on Nov. 3, 1998, U.S. Pat. No. 6,156,892 the entire contents of which are hereby incorporated by reference.

BACKGROUND OF THE INVENTION

1. Field of the Invention

The present invention relates to a purine derivative having a cyclopropane ring, a process for preparing the same, and a process for preparing a cyclopropane ring-cleaved purine derivative from the purine derivative having a cyclopropane ring. The present invention also relates to a process for preparing a cyclopropane ring-cleaved compound.

2. Discussion of the Related Art

Conventionally, as to preparation process for purine derivatives useful for preparation intermediates for antiviral agents, there can be cited, for instance, a process disclosed in Japanese Patent Laid-Open No. Hei 3-120279. However, when the purine derivative is prepared from the preparation intermediates in the above preparation processes, its yield is as low as about 20 to about 40%. In addition, since extremely complicated procedures are necessitated in order to prepare the above preparation intermediates, there is a defect that the purine derivatives cannot be readily prepared as a consequence.

Therefore, recently, a development of a preparation intermediate which can be used in a process which can readily prepare a cyclopropane ring-cleaved purine derivative in a high yield and at high purity has been in demand.

In addition, there has been known to prepare a cyclopropane ring-cleaved compound by a process comprising hydrogenating a compound having a cyclopropane ring in the presence of a metal catalyst by the action of hydrogen gas as a hydrogen source; and cleaving the cyclopropane ring by reduction.

However, in this process, since it has been necessitated to pressurize the reaction system with hydrogen gas to a pressure of 3 to 5 $kgf/cm^2$ upon hydrogenation, there arise such defects that the desired cyclopropane ring-cleaved compound has a low yield owing to the presence of large amounts of by-products in addition to the lack of operability and safety.

In view of the problems in the prior art, an object of the present invention is to provide a process for readily preparing a cyclopropane ring-cleaved purine derivative in a high yield and at high purity, a purine derivative having a cyclopropane ring which can be suitably used in the above process, and a process for preparing the purine derivative having a cyclopropane ring.

Another object of the present invention is to provide a process for preparing a cyclopropane ring-cleaved compound with excellent operability and safety in a high yield.

These and other objects of the present invention will be apparent from the following description.

SUMMARY OF THE INVENTION

The present invention pertains to the following:

(1) a purine derivative having a cyclopropane ring represented by the formula (I):

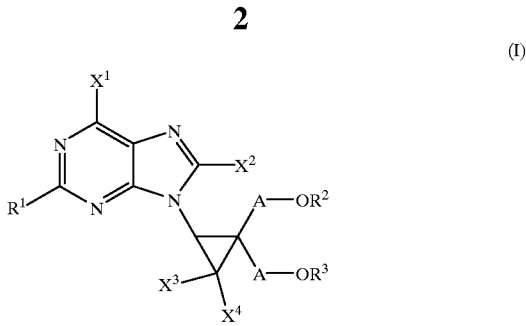

(I)

wherein A is —$CH_2$— group or —CO— group; $X^1$ is hydrogen atom, a halogen atom, an alkoxy group having 1 to 10 carbon atoms, or hydroxyl group; each of $X^2$, $X^3$, and $X^4$ is independently hydrogen atom or a halogen atom; $R^1$ is hydrogen atom, a halogen atom, or a protected or unprotected amino group; and each of $R^2$ and $R^3$ is independently hydrogen atom, a substituted or unsubstituted alkyl group having 1 to 7 carbon atoms, a substituted or unsubstituted aralkyl group having 7 to 11 carbon atoms, or a substituted or unsubstituted acyl group having 1 to 7 carbon atoms, with proviso that in a case where A is —CO— group, neither $R^2$ nor $R^3$ is a substituted or unsubstituted acyl group having 1 to 7 carbon atoms, and each of $X^3$ and $X^4$ is independently a halogen atom;

(2) the purine derivative having a cyclopropane ring according to item (1) above, wherein the purine derivative having a cyclopropane ring represented by the formula (I) is a compound represented by the formula (II):

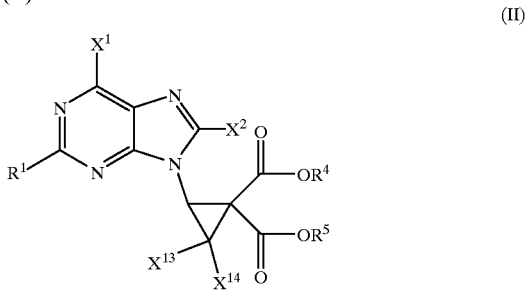

(II)

wherein each of $X^{13}$ and $X^{14}$ is independently a halogen atom; each of $R^4$ and $R^5$ is independently hydrogen atom, a substituted or unsubstituted alkyl group having 1 to 7 carbon atoms, or a substituted or unsubstituted aralkyl group having 7 to 11 carbon atoms; and $X^1$, $X^2$, and $R^1$ are the same as defined above;

(3) the purine derivative having a cyclopropane ring according to item (1) above, wherein the purine derivative having a cyclopropane ring represented by the formula (I) is a compound represented by the formula (III):

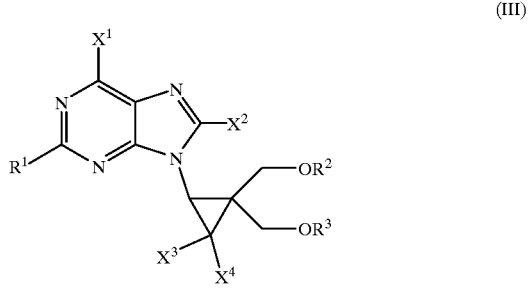

(III)

wherein $X^1$, $X^2$, $X^3$, $X^4$, $R^1$, $R^2$, and $R^3$ are the same as defined above;

(4) the purine derivative having a cyclopropane ring according to item (3) above, wherein the purine derivative having a cyclopropane ring represented by the formula (III) is a compound represented by the formula (IV):

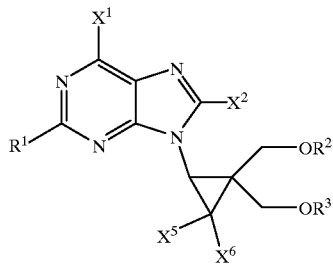

(IV)

wherein each of $X^5$ and $X^6$ is independently a halogen atom; and $X^1$, $X^2$, $R^1$, $R^2$, and $R^3$ are the same as defined above;

(5) the purine derivative having a cyclopropane ring according to item (3) or (4) above, wherein $X^1$ is chlorine atom;

(6) the purine derivative having a cyclopropane ring according to any one of items (3) to (5) above, wherein each of $R^2$ and $R^3$ is hydrogen atom;

(7) the purine derivative having a cyclopropane ring according to any one of items (3) to (5) above, wherein each of $R^2$ and $R^3$ is acetyl group;

(8) a process for preparing a purine derivative having a cyclopropane ring represented by the formula (II):

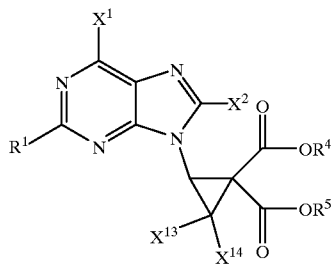

(II)

wherein $X^1$ is hydrogen atom, a halogen atom, an alkoxy group having 1 to 10 carbon atoms, or hydroxyl group; $X^2$ is hydrogen atom or a halogen atom; each of $X^{13}$ and $X^{14}$ is independently a halogen atom; $R^1$ is hydrogen atom, a halogen atom, or a protected or unprotected amino group; and each of $R^4$ and $R^5$ is independently hydrogen atom, a substituted or unsubstituted alkyl group having 1 to 7 carbon atoms, or a substituted or unsubstituted aralkyl group having 7 to 11 carbon atoms, comprising reacting a malonic acid derivative represented by the formula (V):

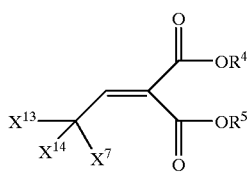

(V)

wherein each of $X^7$, $X^{13}$, and $X^{14}$ is independently a halogen atom; and $R^4$ and $R^5$ are the same as defined above, with a purine compound represented by the formula (VI):

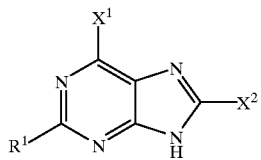

(VI)

wherein $X^1$, $X^2$, and $R^1$ are the same as defined above;

(9) a process for preparing a purine derivative having a cyclopropane ring represented by the formula (IIIa):

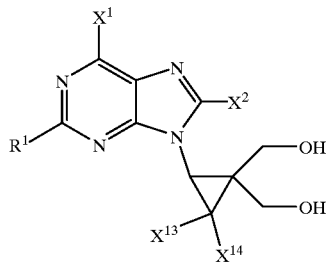

(IIIa)

wherein $X^1$ is hydrogen atom, a halogen atom, an alkoxy group having 1 to 10 carbon atoms, or hydroxyl group; $X^2$ is hydrogen atom or a halogen atom; each of $X^{13}$ and $X^{14}$ is independently a halogen atom; and $R^1$ is hydrogen atom, a halogen atom, or a protected or unprotected amino group, comprising reacting a dicarboxylic acid-based compound represented by the formula (VII):

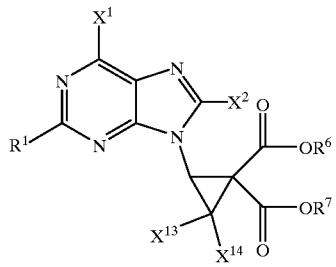

(VII)

wherein each of $R^6$ and $R^7$ is independently a substituted or unsubstituted alkyl group having 1 to 7 carbon atoms; and $X^1$, $X^2$, $X^{13}$, $X^{14}$ and $R^1$ are the same as defined above, with a metal hydride;

(10) a process for preparing a purine derivative having a cyclopropane ring represented by the formula (IIIc):

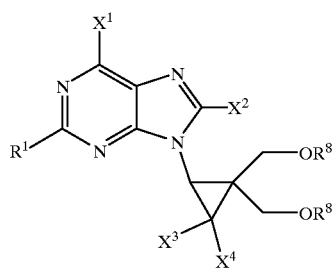

(IIIc)

wherein $X^1$ is hydrogen atom, a halogen atom, an alkoxy group having 1 to 10 carbon atoms, or hydroxyl group; each of $X^2$, $X^3$, and $X^4$ is independently hydrogen atom or a halogen atom; $R^1$ is hydrogen atom, a halogen atom, or a protected or unprotected amino group; and each of $R^8$'s is independently a substituted or unsubstituted alkyl group having 1 to 7 carbon atoms or a substituted or unsubstituted aralkyl group having 7 to 11 carbon atoms,
comprising reacting a purine derivative having a cyclopropane ring represented by the formula (IIIb):

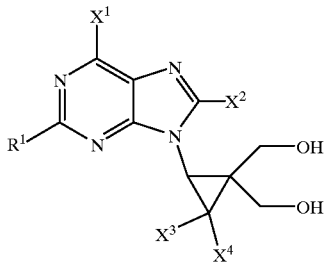

(IIIb)

wherein $X^1$, $X^2$, $X^3$, $X^4$, and $R^1$ are the same as defined above,
with an alkylating agent represented by the formula (VIII):

$$R^8—X^8 \qquad (VIII)$$

wherein $X^8$ is chlorine atom, bromine atom, or iodine atom; and $R^8$ is the same as defined above;

(11) a process for preparing a purine derivative having a cyclopropane ring represented by the formula (IIId):

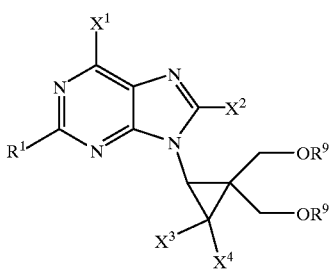

(IIId)

wherein $X^1$ is hydrogen atom, a halogen atom, an alkoxy group having 1 to 10 carbon atoms, or hydroxyl group; each of $X^2$, $X^3$, and $X^4$ is independently hydrogen atom or a halogen atom; $R^1$ is hydrogen atom, a halogen atom, or a protected or unprotected amino group; and each of $R^9$'s is independently a substituted or unsubstituted acyl group having 1 to 7 carbon atoms,
comprising reacting a purine derivative having a cyclopropane ring represented by the formula (IIIb):

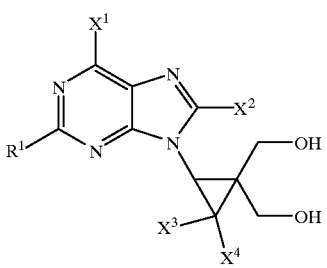

(IIIb)

wherein $X^1$, $X^2$, $X^3$, $X^4$, and $R^1$ are the same as defined above, with a compound represented by the formula (IX):

$$R^9—X^9 \qquad (IX)$$

wherein $X^9$ is hydroxyl group, chlorine atom, bromine atom, or —$OR^9$ group; and $R^9$ is the same as defined above.

(12) a process for preparing a cyclopropane ring-cleaved purine derivative represented by the formula (X):

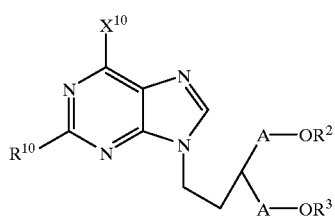

(X)

wherein A is —$CH_2$— group or —CO— group; $X^{10}$ is hydrogen atom, an alkoxy group having 1 to 10 carbon atoms, or hydroxyl group; and each of $R^2$ and $R^3$ is independently hydrogen atom, a substituted or unsubstituted alkyl group having 1 to 7 carbon atoms, a substituted or unsubstituted aralkyl group having 7 to 11 carbon atoms, or a substituted or unsubstituted acyl group having 1 to 7 carbon atoms; and $R^{10}$ is hydrogen atom or a protected or unprotected amino group, with proviso that in a case where A is —CO— group, neither $R^2$ nor $R^3$ is a substituted or unsubstituted acyl group having 1 to 7 carbon atoms, comprising hydrogenating a purine derivative having a cyclopropane ring represented by the formula (I):

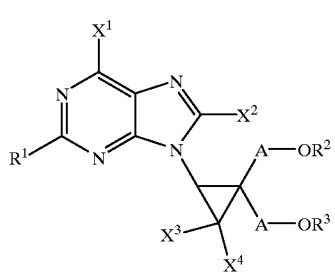

(I)

wherein $X^1$ is hydrogen atom, a halogen atom, an alkoxy group having 1 to 10 carbon atoms, or hydroxyl group; each of $X^2$, $X^3$, and $X^4$ is independently hydrogen atom or a halogen atom; $R^1$ is hydrogen atom, a halogen atom, or a protected or unprotected amino group; and A, $R^2$ and $R^3$ are the same as defined above, with proviso that in a case where A is —CO— group, neither $R^2$ nor $R^3$ is a substituted or unsubstituted acyl group having 1 to 7 carbon atoms, and each of $X^3$ and $X^4$ is independently a halogen atom;

(13) a process for preparing a cyclopropane ring-cleaved compound represented by the formula (XII):

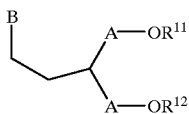

(XII)

wherein A is —CH$_2$— group or —CO— group; B is a nitrogen-containing heterocyclic ring; and each of R$^{11}$ and R$^{12}$ is independently hydrogen atom, a substituted or unsubstituted alkyl group having 1 to 7 carbon atoms, a substituted or unsubstituted aralkyl group having 7 to 11 carbon atoms, or a substituted or unsubstituted acyl group having 1 to 7 carbon atoms, with proviso that in a case where A is —CO— group, neither R$^{11}$ nor R$^{12}$ is a substituted or unsubstituted acyl group having 1 to 7 carbon atoms, comprising reacting a compound having a cyclopropane ring represented by the formula (XI):

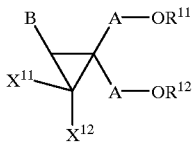

(XI)

wherein each of X$^{11}$ and X$^{12}$ is independently hydrogen atom or a halogen atom; and A, B, R$^{11}$, and R$^{12}$ are the same as defined above, with proviso that in a case where A is —CO— group, neither R$^{11}$ nor R$^{12}$ is a substituted or unsubstituted acyl group having 1 to 7 carbon atoms, and each of X$^{11}$ and X$^{12}$ is independently a halogen atom, with formic acid or a formate in the presence of a catalyst;

(14) the process according to item (13) above, wherein the catalyst is at least one substance selected from the group consisting of palladium, platinum, nickel, and compounds of one of these elements; and

(15) the process according to item (13) or (14) above, wherein the formate is an alkali metal formate.

DETAILED DESCRIPTION OF THE INVENTION

As mentioned above, the purine derivative having a cyclopropane ring of the present invention is a compound represented by the formula (I):

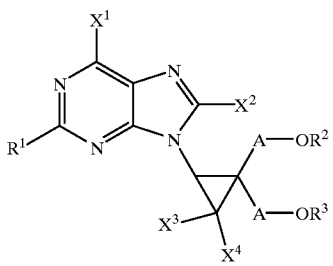

(I)

wherein A is —CH$_2$— group or —CO— group; X$^1$ is hydrogen atom, a halogen atom, an alkoxy group having 1 to 10 carbon atoms, or hydroxyl group; each of X$^2$, X$^3$, and X$^4$ is independently hydrogen atom or a halogen atom; R$^1$ is hydrogen atom, a halogen atom, or a protected or unprotected amino group; each of R$^2$ and R$^3$ is independently hydrogen atom, a substituted or unsubstituted alkyl group having 1 to 7 carbon atoms, a substituted or unsubstituted aralkyl group having 7 to 11 carbon atoms, or a substituted or unsubstituted acyl group having 1 to 7 carbon atoms, with proviso that in a case where A is —CO— group, neither R$^2$ nor R$^3$ is a substituted or unsubstituted acyl group having 1 to 7 carbon atoms, and each of X$^3$ and X$^4$ is independently a halogen atom.

In the formula (I), A is —CH$_2$— group or —CO— group.

X$^1$ is hydrogen atom, a halogen atom, an alkoxy group having 1 to 10 carbon atoms, or hydroxyl group. Examples of the halogen atom include fluorine atom, chlorine atom, bromine atom, and iodine atom, among which a preference is given to chlorine atom, bromine atom, and iodine atom.

Examples of the alkoxy group having 1 to 10 carbon atoms include methoxy group, ethoxy group, propoxy group, benzyloxy group, 2-methyl-2-propoxy group, cyclopentyloxy group, cyclohexyloxy group, and the like.

Each of X$^2$, X$^3$, and X$^4$ is independently hydrogen atom or a halogen atom. Examples of the halogen atom include fluorine atom, chlorine atom, bromine atom, and iodine atom, among which a preference is given to chlorine atom, bromine atom, and iodine atom, with proviso that in a case where A is —CO— group, each of X$^3$ and X$^4$ is independently a halogen atom.

R$^1$ is hydrogen atom, a halogen atom, or a protected or unprotected amino group. Examples of the halogen atom include fluorine atom, chlorine atom, bromine atom, and iodine atom.

Concrete examples of the protected amino group include formylamino group, acetylamino group, benzylamino group, dimethylaminomethyleneamino group, benzyloxycarbonylamino group, and the like.

Each of R$^2$ and R$^3$ is independently hydrogen atom, a substituted or unsubstituted alkyl group having 1 to 7 carbon atoms, a substituted or unsubstituted aralkyl group having 7 to 11 carbon atoms, or a substituted or unsubstituted acyl group having 1 to 7 carbon atoms, with proviso that in a case where A is —CO— group, neither R$^2$ nor R$^3$ is a substituted or unsubstituted acyl group having 1 to 7 carbon atoms.

Examples of the alkyl group having 1 to 7 carbon atoms include methyl group, ethyl group, propyl group, isopropyl group, 2-methylpropyl group, and the like.

Examples of the aralkyl group having 7 to 11 carbon atoms include benzyl group, and the like.

Examples of the acyl group having 1 to 7 carbon atoms include formyl group, acetyl group, benzoyl group, pivaloyl group, and the like.

Examples of the substituent which may be carried by the alkyl group, the aralkyl group, and the acyl group include alkoxy groups having 1 to 6 carbon atoms, such as methoxy group and phenoxy group; hydroxy group; nitro group; amino group; halogen atoms, such as chlorine atom; cyano group, and the like.

In one embodiment where A is —CO— group in the purine derivative having a cyclopropane ring of the present invention represented by the formula (I), the compound is represented by the formula (II):

(II)

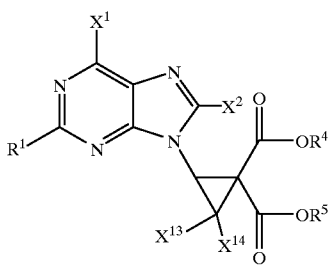

wherein each of $X^{13}$ and $X^{14}$ is independently a halogen atom; each of $R^4$ and $R^5$ is independently hydrogen atom, a substituted or unsubstituted alkyl group having 1 to 7 carbon atoms, or a substituted or unsubstituted aralkyl group having 7 to 11 carbon atoms; and $X^1$, $X^2$, and $R^1$ are the same as defined above.

In each of $R^4$ and $R^5$ above, the substituted or unsubstituted alkyl group having 1 to 7 carbon atoms and the substituted or unsubstituted aralkyl group having 7 to 11 carbon atoms may be the same ones as those exemplified for the substituted or unsubstituted alkyl group having 1 to 7 carbon atoms and the substituted or unsubstituted aralkyl group having 7 to 11 carbon atoms described in $R^2$ and $R^3$ of the formula (I).

In the formula (II), it is desired that each of $X^1$, $X^{13}$, and $X^{14}$ is chlorine atom, bromine atom, or iodine atom; $X^2$ is hydrogen atom; each of $R^4$ and $R^5$ is an alkyl group having 1 to 5 carbon atoms, or hydrogen atom; and $R^1$ is a protected or unprotected amino group. Examples of the alkyl group having 1 to 5 carbon atoms include methyl group, ethyl group, propyl group, isopropyl group, butyl group, pentyl group, and the like.

In addition, in the formula (II), when $R^1$ is a protected or unprotected amino group, examples of the protected group which may be carried by amino group include an acyl group having 1 to 7 carbon atoms, a group represented by $CH_3-N(CH_3)-CH=$, and the like. Examples of the acyl group having 1 to 7 carbon atoms include formyl group, acetyl group, pivaloyl group, benzoyl group, and the like.

The purine derivative having a cyclopropane ring represented by the formula (II) can be prepared by a process comprising reacting a malonic acid derivative represented by the formula (V):

(V)

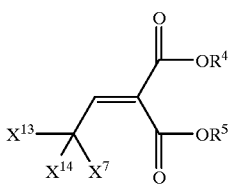

wherein each of $X^7$, $X^{13}$, and $X^{14}$ is independently a halogen atom; and each of $R^4$ and $R^5$ is independently hydrogen atom, a substituted or unsubstituted alkyl group having 1 to 7 carbon atoms, or a substituted or unsubstituted aralkyl group having 7 to 11 carbon atoms, with a purine compound represented by the formula (VI):

(VI)

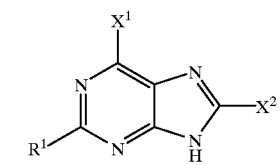

wherein $X^1$ is hydrogen atom, a halogen atom, an alkoxy group having 1 to 10 carbon atoms, or hydroxyl group; $X^2$ is hydrogen atom or a halogen atom; and $R^1$ is hydrogen atom, a halogen atom, or a protected or unprotected amino group.

In the present invention, the reaction of the malonic acid derivative represented by the formula (V) with the purine compound represented by the formula (VI) can be carried out by a process, for instance, comprising adding a purine compound represented by the formula (VI) in advance to a solvent and stirring the resulting mixed solution, and subsequently adding a malonic acid derivative represented by the formula (V) to the resulting mixture.

In the formula (V), it is desired that each of $X^7$, $X^{13}$, and $X^{14}$ is chlorine atom, bromine atom, or iodine atom; and each of $R^4$ and $R^5$ is a substituted or unsubstituted alkyl group having 1 to 5 carbon atoms, or hydrogen atom.

In the formula (VI), it is desired that $X^1$ is chlorine atom, bromine atom, or iodine atom; $X^2$ is hydrogen atom; and $R^1$ is a protected or unprotected amino group.

As to the solvents, there can be cited, for instance, N,N-dimethylformamide, N-methylpyrrolidone, dimethylsulfoxide, and the like, among which N,N-dimethylformamide and dimethylsulfoxide are favorably used from the viewpoints of reactivity and economic advantages.

It is desired that the amount of the solvent is usually from about 500 to about 10000 parts by weight, based on 100 parts by weight of the purine compound represented by the formula (VI).

Incidentally, in the present invention, it is desired that the reaction of the malonic acid derivative represented by the formula (V) with the purine compound represented by the formula (VI) is carried out in the presence of a base having weak nucleophilic property. Typical examples of the base having weak nucleophilic property include alkali metal carbonates.

Examples of the alkali metal carbonates include potassium carbonate, sodium carbonate, rubidium carbonate, cesium carbonate, and the like, among which potassium carbonate can be favorably used from the viewpoint of the reactivity.

It is desired that the amount of the alkali metal carbonate is usually 0.5 mol or more, preferably one mol or more, per one mol of the purine compound represented by the formula (VI) in order to expedite the progress of the reaction, and that the amount of the alkali metal carbonate is 20 mol or less, preferably 5 mol or less, per one mol of the purine compound represented by the formula (VI), from the viewpoint of economic advantages.

The alkali metal carbonate can be used by adding to the solvent together with the purine compound represented by the formula (VI).

It is desired that the amount of the malonic acid derivative represented by the formula (V) is usually one mol or more, preferably 1.1 mol or more, per one mol of the purine compound represented by the formula (VI), since one mol of the malonic acid derivative is theoretically needed to one mol of the purine compound. It is also desired that the amount of the malonic acid derivative is 50 mol or less, preferably 5 mol or less, per one mol of the purine compound represented by the formula (VI), from the viewpoint of economic advantages.

The malonic acid derivative represented by the formula (V) can be readily prepared by a process, for instance, disclosed in U.S. Pat. No. 3,495,012.

The atmosphere in which the reaction of the malonic acid derivative represented by the formula (V) with the purine compound represented by the formula (VI) is carried out is not limited to specified ones, and the atmosphere may be preferably air, or an inert gas atmosphere such as nitrogen gas, and argon gas. It is also desired that the reaction temperature is usually from about —10° to about 100° C., preferably from about 0° to about 60° C.

The reaction time cannot be absolutely determined because the reaction time can differ depending upon the reaction temperature, and the like. The reaction time may be preferably a length of time sufficient to terminate the reaction, and the reaction time is usually from 0.5 to 5 hours or so.

The termination of the reaction can be confirmed, for instance, by high-performance liquid chromatography, or the like.

After the termination of reaction, the resulting purine derivative having a cyclopropane ring represented by the formula (II) can be isolated by carrying out such procedures including filtration, precipitation, washing, concentration, and the like.

Thus, the purine derivative having a cyclopropane ring represented by the formula (II) can be readily prepared.

In another embodiment where A is —CH$_2$— group in the purine derivative having a cyclopropane ring in the formula (I), the compound is represented by the formula (III):

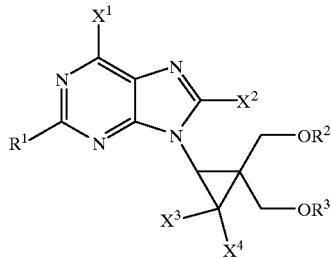

(III)

wherein $X^1$, $X^2$, $X^3$, $X^4$, $R^1$, $R^2$, and $R^3$ are the same as defined above.

In the present invention, among the purine derivatives having a cyclopropane ring represented by the formula (III), the purine derivative having a cyclopropane ring represented by the formula (IV):

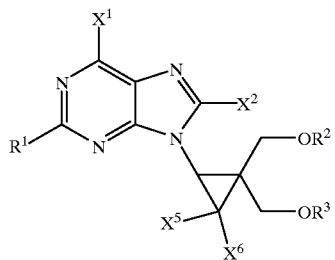

(IV)

wherein each of $X^5$ and $X^6$ is independently a halogen atom; and $X^1$, $X^2$, $R^1$, $R^2$, and $R^3$ are the same as defined above, is preferable. Among them, the compounds where $X^1$ is chlorine atom, and the compounds where each of $R^1$ and $R^2$ is hydrogen atom or acetyl group are particularly favorably used as preparation intermediates for antiviral agents.

In $X^5$ and $X^6$ above, examples of the halogen atom include fluorine atom, chlorine atom, bromine atom, and iodine atom, among which a preference is given to chlorine atom, bromine atom, and iodine atom.

A compound where each of $R^2$ and $R^3$ is hydrogen atom and each of $X^3$ and $X^4$ is a halogen atom in the purine derivative having a cyclopropane ring represented by the formula (III), namely a purine derivative having a cyclopropane ring represented by the formula (IIIa):

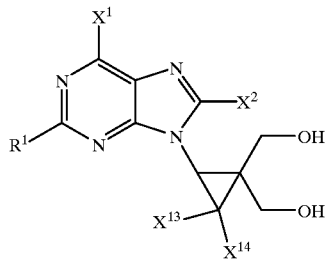

(IIIa)

wherein $X^1$, $X^2$, $X^{13}$, $X^{14}$, and $R^1$ are the same as defined above, can be prepared by a process comprising reacting a dicarboxylic acid-based compound represented by the formula (VII):

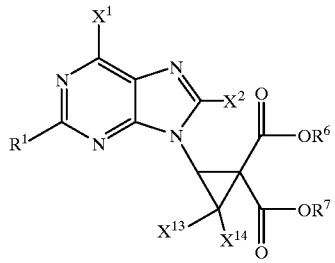

(VII)

wherein each of $R^6$ and $R^7$ is independently a substituted or unsubstituted alkyl group having 1 to 7 carbon atoms; and $X^1$, $X^2$, $X^{13}$, $X^{14}$, and $R^1$ are the same as defined above, with a metal hydride.

In each of $R^6$ and $R^7$, the substituted or unsubstituted alkyl group having 1 to 7 carbon atoms may be the same ones as those exemplified for the substituted or unsubstituted alkyl group having 1 to 7 carbon atoms described in $R^2$ and $R^3$ of the formula (I).

The reaction of the dicarboxylic acid-based compound represented by the formula (VII) with the metal hydride can be carried out by a process, for instance, comprising dissolving or suspending a dicarboxylic acid-based compound represented by the formula (VII) in a solvent, and adding a metal hydride to the resulting mixture.

The dicarboxylic acid-based compound represented by the formula (VII) can be prepared by a process disclosed, for instance, in Japanese Patent Laid-Open No. Hei 3-120279.

Examples of the metal hydride include sodium borohydride, borane, lithium aluminum hydride, diisobutylaluminum hydride, lithium borohydride, and the like.

Since 4 mol of hydride ions is theoretically required to one mol of the dicarboxylic acid-based compound represented by the formula (VII), it is desired that the amount of the metal hydride is adjusted such that the amount of the hydride ions is 4 mol or more, preferably 6 mol or more, to one mol of the dicarboxylic acid-based compound represented by the formula (VII). From the viewpoint of economic advantages, it is desired that the amount of the metal hydride is adjusted such that the amount of the hydride ions is 30 mol or less, preferably 20 mol or less, to one mol of the dicarboxylic acid-based compound represented by the formula (VII).

Examples of the solvent include polar solvents such as N,N-dimethylformamide and 1,3-dimethyl-2-imidazolidinone; alcohols such as methanol, ethanol, 2-propanol, and 2-methyl-2-propanol; ethers such as tetrahydrofuran, and the like. It is desired that the amount of the solvent is adjusted such that the amount of the dicarboxylic acid-based compound represented by the formula (VII) is usually from 1 to 50 parts by weight, based on 100 parts by weight of the solvent.

It is desired that the temperature upon the reaction of the dicarboxylic acid-based compound represented by the formula (VII) with the metal hydride is usually 0° to 50° C. or so. The atmosphere may be an air or an inert gas such as nitrogen gas.

The reaction time cannot be absolutely determined because the reaction time can differ depending upon the reaction temperature, and the like. The reaction time may be preferably a length of time sufficient to terminate the reaction, and the reaction time is usually from 0.5 to 5 hours or so. The termination of the reaction can be confirmed, for instance, by high-performance liquid chromatography, or the like.

A compound where each of $R^2$ and $R^3$ is a substituted or unsubstituted alkyl group having 1 to 7 carbon atoms or a substituted or unsubstituted aralkyl group having 7 to 11 carbon atoms in the purine derivative having a cyclopropane ring represented by the formula (III), namely a purine derivative having a cyclopropane ring represented by the formula (IIIc):

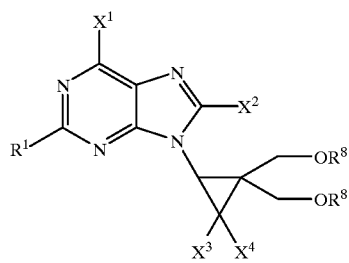

(IIIc)

wherein each of $R^8+$ is independently a substituted or unsubstituted alkyl group having 1 to 7 carbon atoms or a substituted or unsubstituted aralkyl group having 7 to 11 carbon atoms; and $X^1$, $X^2$, $X^3$, $X^4$, and $R^1$ are the same as defined above, can be prepared by a process comprising reacting a purine derivative having a cyclopropane ring represented by the formula (IIIb):

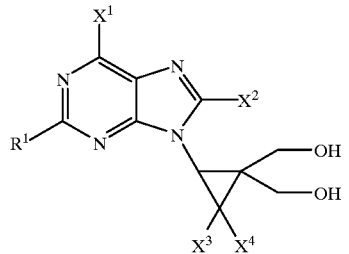

(IIIb)

wherein $X^1$, $X^2$, $X^3$, $X^4$, and $R^1$ are the same as defined above, with an alkylating agent represented by the formula (VIII):

$$R^8—X^8 \qquad (VIII)$$

wherein $X^8$ is chlorine atom, bromine atom, or iodine atom; and $R^8$ is the same as defined above.

In $R^8$ above, the substituted or unsubstituted alkyl group having 1 to 7 carbon atoms and the substituted or unsubstituted aralkyl group having 7 to 11 carbon atoms may be the same ones as those exemplified for the substituted or unsubstituted alkyl group having 1 to 7 carbon atoms and the substituted or unsubstituted aralkyl group having 7 to 11 carbon atoms described in $R^2$ and $R^3$ of the formula (I).

The reaction of the purine derivative having a cyclopropane ring represented by the formula (IIIb) with the alkylating agent represented by the formula (VIII) can be carried out by a process, for instance, comprising dissolving a purine derivative having a cyclopropane ring represented by the formula (IIIb) in a solvent, and adding an alkylating agent to the resulting mixture.

Since 2 mol of the alkylating agent represented by the formula (VIII) is theoretically required to one mol of the purine derivative having a cyclopropane ring represented by the formula (IIIb), it is desired that the amount of the alkylating agent is 2 mol or more, preferably 2.2 mol or more, per one mol of the purine derivative having a cyclopropane ring represented by the formula (IIIb). From the viewpoint of economic advantages, it is desired that the amount of the alkylating agent is 10 mol or less, preferably 4 mol or less, per one mol of the purine derivative having a cyclopropane ring represented by the formula (IIIb).

Examples of the solvent include esters such as ethyl acetate; ethers such as tetrahydrofuran; nitriles such as acetonitrile; aromatic hydrocarbons such as toluene, and the like. It is desired that the amount of the solvent is adjusted such that the amount of the purine derivative having a cyclopropane ring represented by the formula (IIIb) is usually from 1 to 50 parts by weight, based on 100 parts by weight of the solvent.

It is desired that the temperature upon the reaction of the purine derivative having a cyclopropane ring represented by the formula (IIIb) with the alkylating agent represented by the formula (VIII) is usually 10° to 80° C. or so. The atmosphere may be an air or an inert gas such as nitrogen gas.

The reaction time cannot be absolutely determined because the reaction time can differ depending upon the reaction temperature, and the like. The reaction time may be preferably a length of time sufficient to terminate the reaction, and the reaction time is usually from 1.5 to 8 hours or so. The termination of the reaction can be confirmed, for instance, by high-performance liquid chromatography, or the like.

A compound where each of $R^2$ and $R^3$ is a substituted or unsubstituted acyl group having 1 to 7 carbon atoms in the purine derivative having a cyclopropane ring represented by the formula (III), namely a purine derivative having a cyclopropane ring represented by the formula (IIId):

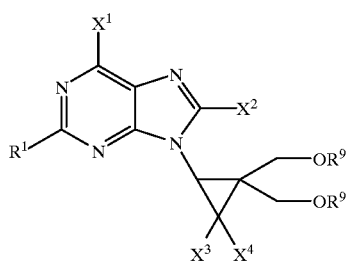

(IIId)

wherein each of $R^9$'s is independently a substituted or unsubstituted acyl group having 1 to 7 carbon atoms; and $X^1$, $X^2$, $X^3$, $X^4$, and $R^1$ are the same as defined above, can be prepared by a process comprising reacting a purine derivative having a cyclopropane ring represented by the formula (IIIb) with a compound represented by the formula (IX):

$R^9$—$X^9$ (IX)

wherein $X^9$ is hydroxyl group, chlorine atom, bromine atom, or —$OR^9$ group; and $R^9$ is the same as defined above.

In $R^9$ above, the substituted or unsubstituted acyl group having 1 to 7 carbon atoms may be the same ones as those exemplified for the substituted or unsubstituted acyl group having 1 to 7 carbon atoms described in $R^2$ and $R^3$ of the formula (I).

$X^9$ is hydroxyl group, chlorine atom, bromine atom, or —$OR^9$ group; and $R^9$ is the same as defined above.

The reaction of the purine derivative having a cyclopropane ring represented by the formula (IIIb) with the compound represented by the formula (IX) can be carried out by a process, for instance, comprising suspending a purine derivative having a cyclopropane ring represented by the formula (IIIb) in a solvent, adding a base to the resulting suspension, and subsequently adding a compound represented by the formula (IX) to the resulting mixture.

Since 2 mol of the compound represented by the formula (IX) is theoretically required to one mol of the purine derivative having a cyclopropane ring represented by the formula (IIIb), it is desired that the amount of the compound represented by the formula (XI) is 2 mol or more, preferably 2.2 mol or more, per one mol of the purine derivative having a cyclopropane ring represented by the formula (IIIb). From the viewpoint of economic advantages, it is desired that the amount of the compound represented by the formula (XI) is 10 mol or less, preferably 4 mol or less, per one mol of the purine derivative having a cyclopropane ring represented by the formula (IIIb).

Examples of the base include nitrogen-containing heterocyclic compounds such as pyridine, 4-dimethylaminopyridine, imidazole, and diazabicycloundecene; tertiary amines such as triethylamine and diisopropylethylamine, and the like. Those bases may be used alone or in an admixture thereof. It is desired that the amount of the base is equal to or more than the stoichiometric amount to one mol of the purine derivative having a cyclopropane ring represented by the formula (IIIb), namely 2 mol or more, preferably 2.2 mol or more.

Examples of the solvent include esters such as ethyl acetate; ethers such as tetrahydrofuran; nitrites such as acetonitrile; aromatic hydrocarbons such as toluene, and the like. It is desired that the amount of the solvent is adjusted such that the amount of the purine derivative having a cyclopropane ring represented by the formula (IIIb) is usually from 1 to 50 parts by weight, based on 100 parts by weight of the solvent.

It is desired that the temperature upon the reaction of the purine derivative having a cyclopropane ring represented by the formula (IIIb) with the compound represented by the formula (IX) is usually 0° to 80° C. or so. The atmosphere may be an air or an inert gas such as nitrogen gas.

The reaction time cannot be absolutely determined because the reaction time can differ depending upon the reaction temperature, and the like. The reaction time may be preferably a length of time sufficient to terminate the reaction, and the reaction time is usually from 0.5 to 5 hours or so. The termination of the reaction can be confirmed, for instance, by high-performance liquid chromatography, or the like.

The purine derivative having a cyclopropane ring represented by the formula (I) as described above is a novel compound, and it can be favorably used for preparation intermediates for a cyclopropane ring-cleaved purine derivative represented by the formula (X):

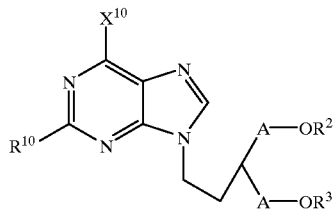

(X)

wherein $X^{10}$ is hydrogen atom, an alkoxy group having 1 to 10 carbon atoms, or hydroxyl group; $R^{10}$ is hydrogen atom or a protected or unprotected amino group; and A, $R^2$, and $R^3$ are the same as defined above, with proviso that in a case where A is —CO— group, neither $R^2$ nor $R^3$ is a substituted or unsubstituted acyl group having 1 to 7 carbon atoms, which can be used for preparation intermediates for antiviral agents as disclosed in, for instance, *"Nucleoside Nucleotide,"* 15[5] (1996), 981–994; Japanese Examined Patent Publication No. Hei 5-86792, and the like.

In $X^{10}$ above, the alkoxy group having 1 to 10 carbon atoms may be the same ones as those exemplified for the alkoxy group having 1 to 10 carbon atoms described in $X^1$ of the formula (I).

In $R^{10}$ above, the protected or unprotected amyl group may be the same ones as those exemplified for the protected or unprotected amyl group described in $R^1$ of the formula (I).

In the present invention, the cyclopropane ring-cleaved purine derivative represented by the formula (X) can be prepared by a process comprising hydrogenating a purine derivative having a cyclopropane ring represented by the formula (I).

There are, for instance, two embodiments of processes for hydrogenating a purine derivative having a cyclopropane ring represented by the formula (I).

Embodiment (A): a process for catalytically reducing a purine derivative having a cyclopropane ring represented by the formula (I).

Embodiment (B): a process for reacting a purine derivative having a cyclopropane ring represented by the formula (I) with formic acid or a formate.

Among Embodiments (A) and (B), Embodiment (B) is preferably employed from the viewpoints of reactivity and operability.

In Embodiment (A), the catalytic reduction of the purine derivative having a cyclopropane ring represented by the formula (I) can be carried out by a process, for instance, comprising suspending a purine derivative having a cyclopropane ring represented by the formula (I) and a catalyst in a solvent to prepare a suspension, and shaking or stirring the resulting suspension in a hydrogen gas atmosphere, or blowing hydrogen gas into the suspension.

Examples of the catalyst include palladium, platinum, nickel, or compounds of one of these elements. Examples of such compounds include hydroxides such as palladium hydroxide; oxides such as platinum oxide; Raney nickel and Raney cobalt; metallic catalysts such as palladium black, platinum black, and the like. Those catalysts may be used alone or they may be used in the form of carrier catalysts in which the catalyst is carried on a carbon, the carrier catalysts including palladium-carbon, platinum-carbon, or the like. Among those catalysts, from the viewpoints of availability and reactivity, palladium-carbon, platinum-carbon, palladium black, palladium hydroxide, and Raney nickel are preferably employed.

It is desired that the amount of the catalyst is 1 part by weight or more, preferably 20 parts by weight or more, more preferably 30 parts by weight or more, based on 100 parts by weight of the purine derivative having a cyclopropane ring represented by the formula (I), in order to expedite the progress of the reaction, and that the amount of the catalyst is 200 parts by weight or less, preferably 100 parts by weight or less, more preferably 50 parts by weight or less, based on 100 parts by weight of the purine derivative having a cyclopropane ring represented by the formula (I), from the viewpoint of economic advantages.

Examples of the solvent include alcohols such as methanol, ethanol, and 2-propanol; ethers such as tetrahydrofuran; organic acids such as acetic acid; esters such as ethyl acetate; polar solvents such as N,N-dimethylformamide; water, and the like. Those solvents may be used alone or in an admixture of two or more kinds.

It is desired that the amount of the solvent is adjusted such that the amount of the purine derivative having a cyclopropane ring represented by the formula. (I) is usually from about 1 to about 100 parts by weight, preferably from about 1 to about 50 parts by weight, more preferably from about 5 to about 30 parts by weight, still more preferably from about 2 to about 10 parts by weight, based on 100 parts by weight of the solvent.

It is desired that the reaction temperature upon catalytic reduction of the purine derivative having a cyclopropane ring represented by the formula (I) is usually from 0° to 200° C. or so, preferably from 0° to 130° C. or so, more preferably from 50° to 90° C. or so, still more preferably from 700 to 90° C. or so. In addition, in a case where the suspension of the purine derivative having a cyclopropane ring represented by the formula (I) is shaken or stirred in a hydrogen gas atmosphere, it is desired that the hydrogen gas pressure is usually from 0 to 20 kgf/cm$^2$ or so, preferably from 0 to 10 kgf/cm$^2$ or so, more preferably from 1 to 7 kgf/cm$^2$ or so, still more preferably from 3 to 7 kgf/cm$^2$ or so.

The reaction time cannot be absolutely determined because the reaction time can differ depending upon the reaction temperature, and the like. The reaction time may be preferably a length of time sufficient to terminate the reaction, and the reaction time is usually from 0.5 to 8 hours or so, preferably from 4 to 7 hours or so. The termination of the reaction can be confirmed, for instance, by high-performance liquid chromatography, or the like.

After the termination of reaction, the resulting cyclopropane ring-cleaved purine derivative represented by the formula (X) can be collected by such separation procedures including, for instance, filtration, concentration, extraction, purification, and the like.

On the other hand, in Embodiment (B), the reaction of the purine derivative having a cyclopropane ring represented by the formula (I) with formic acid or a formate can be carried out by a process, for instance, comprising adding a purine derivative having a cyclopropane ring represented by the formula (I) and a catalyst to a solvent, and subsequently adding a formic acid or a formate to the resulting mixture.

As to the catalyst, the same catalysts as those employed in the catalytic reduction in Embodiment (A) can be employed. It is desired that the amount of the catalyst is usually 0.1 parts by weight or more, preferably 10 parts by weight or more, based on 100 parts by weight of the purine derivative having a cyclopropane ring represented by the formula (I), in order to expedite the progress of the reaction, and that the amount of the catalyst is 100 parts by weight or less, preferably 50 parts by weight or less, based on 100 parts by weight of the purine derivative having a cyclopropane ring represented by the formula (I), from the viewpoint of economic advantages.

Examples of the solvent include water; alcohols such as methanol, ethanol, and isopropanol; ethers such as tetrahydrofuran; esters such as ethyl acetate; polar solvents such as N,N-dimethylformamide; and the like. Those solvents may be used alone or in an admixture of two or more kinds. It is desired that the amount of the solvent is adjusted such that the amount of the purine derivative having a cyclopropane ring represented by the formula (I) is from about 1 to about 50 parts by weight, based on 100 parts by weight of the solvent.

Examples of the formate include alkali metal formates such as sodium formate and potassium formate, ammonium formate, triethylammonium formate, and the like. Among them, from the viewpoints of economic advantages, operability, and shortening the reaction time, a preference is given to the alkali metal formates such as sodium formate and potassium formate.

It is desired that the amount of formic acid or the formate is one mol or more, preferably 1.5 mol or more, per one mol of the purine derivative having a cyclopropane ring represented by the formula (I), in order to complete the reaction. It is also desired that the amount of formic acid or the formate is 20 mol or less, preferably 10 mol or less, per one mol of the purine derivative having a cyclopropane ring represented by the formula (I), from the viewpoint of economic advantages.

It is desired that the reaction temperature upon the reaction of the purine derivative having a cyclopropane ring represented by the formula (I) with formic acid or a formate is usually from 0° to 150° C., preferably from 200 to 80° C. In addition, the atmosphere upon reaction is not limited to specified ones, and the atmosphere may be preferably an inert gas atmosphere or a hydrogen gas atmosphere. Incidentally, the reaction is not necessarily carried out in a pressurized reaction system, and the reaction can be carried out under an ambient pressure.

The reaction time cannot be absolutely determined because the reaction time can differ depending upon the reaction temperature, and the like. The reaction time may be preferably a length of time sufficient to terminate the reaction. It is desired that the reaction time is usually from 1 to 20 hours or so, preferably 1 to 10 hours or so. The termination of the reaction can be confirmed, for instance, by the confirmation of the disappearance of the starting materials by high-performance liquid chromatography, or the like.

After the termination of reaction, the resulting cyclopropane ring-cleaved purine derivative represented by the formula (X) can be collected by such conventional separation procedures including, for instance, filtration, concentration, extraction, purification, and the like.

The resulting cyclopropane ring-cleaved purine derivative represented by the formula (X) as prepared above can be further recrystallized from, for instance, 2-propanol, or the like as occasion demands.

A compound where A is —CO— group in the cyclopropane ring-cleaved purine derivative represented by the formula (X) as prepared by the process of the present invention is extremely useful for preparation intermediates for antiviral agents such as Famciclovir and Penciclovir. In addition, a compound where A is —CH$_2$— group in which a cyclopropane ring-cleaved purine derivative represented by the formula (X) is useful for antiviral agents. In particular, a compound where each of $R^2$ and $R^3$ is acetyl group in the formula (X) is an excellent antiviral agent known as Famciclovir.

Further, according to the present invention, a cyclopropane ring-cleaved compound represented by the formula (XII):

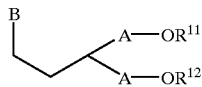

(XII)

wherein A is —CH$_2$— group or —CO— group; B is a nitrogen-containing heterocyclic ring; each of $R^{11}$ and $R^{12}$ is independently hydrogen atom, a substituted or unsubstituted alkyl group having 1 to 7 carbon atoms, a substituted or unsubstituted aralkyl group having 7 to 11 carbon atoms, or a substituted or unsubstituted acyl group having 1 to 7 carbon atoms, with proviso that in a case where A is —CO— group, neither $R^{11}$ nor $R^{12}$ is a substituted or unsubstituted acyl group having 1 to 7 carbon atoms, can be prepared by a process comprising reacting a compound having a cyclopropane ring represented by the formula (XI):

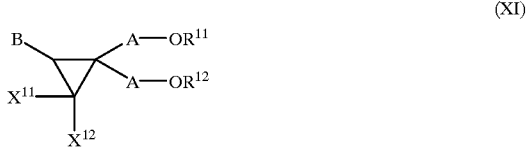

(XI)

wherein each of $X^{11}$ and $X^{12}$ is independently hydrogen atom or a halogen atom; and A, B, $R^{11}$, and $R^{12}$ are the same as defined above, with proviso that in a case where in a case where A is —CO— group, neither $R^{11}$ nor $R^{12}$ is a substituted or unsubstituted acyl group having 1 to 7 carbon atoms, and each of $X^{11}$ and $X^{12}$ is independently a halogen atom, with formic acid or a formate in the presence of a catalyst.

In the compound having a cyclopropane ring represented by the formula (XI), A is —CH$_2$— group or —CO— group.

B is a nitrogen-containing heterocyclic ring. The nitrogen-containing heterocyclic ring in the present invention may be, for instance, a modified or unmodified, substituted or unsubstituted purine ring or pyrimidine ring, and the like. Typical examples of the modified or unmodified, substituted or unsubstituted purine ring and pyrimidine ring include purine rings and pyrimidine rings of which hydrogen atom may be substituted by at least one substituent selected from the group consisting of a halogen atom, hydroxyl group, an alkyl group having 1 to 20 carbon atoms, an alkoxy group having 1 to 20 carbon atoms, an aralkyloxy group having 7 to 20 carbon atoms, and a protected or unprotected amino group. Here, examples of the alkyl group having 1 to 20 carbon atoms include methyl group, ethyl group, isopropyl group, and the like. Examples of the alkoxy group 1 to 20 carbon atoms include methoxy group, ethoxy group, cyclohexyloxy group, menthyloxy group, and the like. Examples of the aralkyloxy group having 7 to 20 carbon atoms include benzyloxy group, trityloxy group, and the like.

Concrete examples of the modified or unmodified, substituted or unsubstituted purine ring and pyrimidine ring in the present invention include 2,4-pyrimidinedionyl group, 4-amino-2-pyrimidinonyl group, 5-methyl-2,4-pyrimidinedionyl group, 2-aminopurinyl group, 6-aminopurinyl group, 2-amino-6-hydroxypurinyl group, 2,6-diaminopurinyl group, 2-amino-6-chloropurinyl group, 2-amino-6-iodopurinyl group, 2-amino-6-methoxypurinyl group, 2-amino-6-benzyloxypurinyl group, 2,6-dichloropurinyl group, and the like.

Each of $X^{11}$ and $X^{12}$ is independently hydrogen atom or a halogen atom, with proviso that in a case where A is —CO— group, each of $X^{11}$ and $X^{12}$ is independently a halogen atom. Examples of the halogen atom include fluorine atom, chlorine atom, bromine atom, and iodine atom, among which a preference is given to chlorine atom, bromine atom, and iodine atom.

Each of $R^{11}$ and $R^{12}$ is independently hydrogen atom, a substituted or unsubstituted alkyl group having 1 to 7 carbon atoms, a substituted or unsubstituted. aralkyl group having 7 to 11 carbon atoms, or a substituted or unsubstituted acyl group having 1 to 7 carbon atoms, with proviso that in a case where A is —CO— group, neither. $R^{11}$ nor $R^{12}$ is a substituted or unsubstituted acyl group having 1 to 7 carbon atoms.

Examples of the alkyl group having 1 to 7 carbon atoms, preferably an alkyl group having 1 to 6 carbon atoms, include methyl group, ethyl group, propyl group, isopropyl group, 2-methylpropyl group, and the like.

Examples of the aralkyl group having 7 to 11 carbon atoms include benzyl group, and the like.

Examples of the acyl group having 1 to 7 carbon atoms include formyl group, acetyl group, propionyl group, benzoyl group, pivaloyl group, and the like.

Examples of the substituent which may be carried by the alkyl group, the aralkyl group, and the acyl group include alkoxy groups having 1 to 6 carbon atoms, such as methoxy group and phenoxy group; hydroxy group; nitro group; amino group; halogen atoms, such as chlorine atom; cyano group, and the like.

In the formula (XI), it is desired that each of $X^{11}$ and $X^{12}$ is independently hydrogen atom, chlorine atom, bromine atom, and iodine atom, and that each of $R^{11}$ and $R^{12}$ is independently hydrogen atom, an alkyl group having 1 to 6 carbon atoms, or an acyl group having 1 to 7 carbon atoms.

Typical examples of the compound having a cyclopropane ring represented by the formula (XI) include 2-amino-6-chloro-9-(3,3-dicarbomethoxy-2,2-dichlorocyclopropyl) purine, 2-amino-9-(3,3-dicarbomethoxycyclopropyl)purine, 2-amino-6-chloro-9-3,3-dicarbomethoxycyclopropyl) purine, 2-amino-9-( 3,3-dicarbomethoxy-2,2-dichlorocyclopropyl)-6-methoxypurine, 2-amino-6-benzyloxy-9-(3, 3-dicarbomethoxy-2,2-dichlorocyclopropyl)purine, 2-amino-9-(3,3-dicarbomethoxy-2,2-dichlorocyclopropyl)-6-chloropurine, 2-amino-9-(3,3-dicarboisopropoxy-2,2-dichlorocyclopropyl)-6-chloropurine, and the like.

The compound having a cyclopropane ring represented by the formula (XI) can be prepared by processes described, for instance, in Japanese Patent Laid-Open No. Hei 3-120279 and Japanese Patent Application No. Hei 9-310839.

In the present invention, the reaction of the compound having a cyclopropane ring represented by the formula (XI) with formic acid or a formate can be carried out by a process, for instance, comprising adding a compound having a cyclopropane ring represented by the formula (XI) and a catalyst to a solvent, and adding formic acid or a formate to the resulting mixture.

Examples of the catalyst include palladium, platinum, nickel, or compounds of one of these elements. Those catalysts may be used alone or in admixture of two or more kinds. Examples of compounds of one of those elements include hydroxides such as palladium hydroxide; oxides such as platinum oxide; Raney nickel and Raney cobalt; metallic catalysts such as palladium black, platinum black, and the like. Those catalysts may be used alone or they may be used in the form of carrier catalysts in which the catalyst is carried on a carbon, the carrier catalysts including palladium-carbon, platinum-carbon, or the like. Among those catalysts, from the viewpoints of availability and reactivity, palladium-carbon, platinum-carbon, palladium black, palladium hydroxide, and Raney nickel are preferably employed.

It is desired that the amount of the catalyst is 0.1 parts by weight or more, preferably 10 parts by weight or more, based on 100 parts by weight of the compound having a cyclopropane ring represented by the formula (XI), in order to expedite the progress of the reaction, and that the amount of the catalyst is 100 parts by weight or less, preferably 50 parts by weight or less, based on 100 parts by weight of the compound having a cyclopropane ring represented by the formula (XI), from the viewpoint of economic advantages.

The solvent is not limited to specified ones, and examples thereof include water; alcohols such as methanol, ethanol, and isopropanol; ethers such as tetrahydrofuran; esters such as ethyl acetate; polar solvents such as N,N-dimethylformamide; and the like. Those solvents may be used alone or in an admixture of two or more kinds. It is desired that the amount of the solvent is adjusted such that the amount of the compound having a cyclopropane ring represented by the formula (XI) is from about 1 to about 50 parts by weight, based on 100 parts by weight of the solvent.

One feature of the present invention resides in the use of formic acid or a formate. In the case where formic acid or a formate is used, it is not necessitated to pressurize the reaction system with hydrogen gas as conventionally required, and excellent effects can be exhibited in the efficient hydrogenation of the compound having a cyclopropane ring represented by the formula (XI), so that the desired cyclopropane ring-cleaved compound represented by the formula (XII) can be prepared safely with good operability and in high yield.

Examples of the formate include alkali metal formates such as sodium formate and potassium formate, ammonium formate, barium formate, triethylammonium formate, and the like. Among them, from the viewpoints of economic advantages, operability, and shortening the reaction time, a preference is given to the alkali metal formates such as sodium formate and potassium formate.

It is desired that the amount of formic acid or the formate is one mol or more, preferably 1.5 mol or more, per one mol of the compound having a cyclopropane ring represented by the formula (XI), in order to complete the reaction. It is also desired that the amount of formic acid or the formate is 20 mol or less, preferably 10 mol or less, per one mol of the compound having a cyclopropane ring represented by the formula (XI), from the viewpoint of economic advantages.

In the present invention, the reaction of the compound having a cyclopropane ring represented by the formula (XI) with formic acid or the formate is not necessarily carried out in a pressurized reaction system as described above, but the reaction can be carried out under an ambient pressure.

It is desired that the reaction temperature upon the reaction of the compound having a cyclopropane ring represented by the formula (XI) with formic acid or a formate is usually from 0° to 150° C., preferably from 20° to 80° C. In addition, the atmosphere upon reaction is not limited to specified ones, and the atmosphere may be preferably an inert gas atmosphere or a hydrogen gas atmosphere.

The reaction time cannot be absolutely determined because the reaction time can differ depending upon the reaction conditions such as the reaction temperature, and the like. The reaction time may be preferably a length of time sufficient to terminate the reaction. It is desired that the reaction time is usually from 1 to 20 hours or so, preferably 1 to 10 hours or so. The termination of the reaction can be confirmed, for instance, by the disappearance of the starting materials by the confirmation of high-performance liquid chromatography, or the like.

After the termination of reaction, the cyclopropane ring-cleaved compound represented by the formula (XII) can be collected . Therefore, the inorganic salts can be removed from the resulting reaction mixture by a process comprising by conventional separation procedures, including, for instance, filtration, concentration, extraction, purification, and the like.

The resulting cyclopropane ring-cleaved compound represented by the formula (XII) as prepared above can be further recrystallized from, for instance, 2-propanol, or the like as occasion demands.

The resulting cyclopropane ring-cleaved compound represented by the formula (XII) can be favorably used for efficiently preparing preparation intermediates for antiviral agents as disclosed in, for instance, "Nucleoside Nucleotide," 15[5] (1996), 981–994; Japanese Examined Patent Publication No. Hei 5-86792, and the like.

EXAMPLES

The present invention will be more specifically described by the following examples, without intending to restrict the scope or spirit of the present invention thereto.

Example I-1

In a 0.3-liter four-necked flask, 7.06 g (41.6 mmol) of 2-amino-6-chloropurine (manufactured by Sumika Fine Chemicals Co., Ltd.) and 12.4 g (89.7 mmol) of potassium carbonate were added to 188 ml of N,N-dimethylformamide, and the resulting mixture was stirred at room temperature for 30 minutes. Next, 16.0 g (61.2 mmol) of dimethyl 2,2,2-trichloroethylidenemalonate, which was prepared by the process described in U.S. Pat. No. 3,495,012, was added to the resulting mixture, and the mixture was stirred for four hours at room temperature. Thereafter, the reaction mixture was filtered, and the filtrate was poured into water. The precipitated crystals were collected by filtration, washed with 100 ml of water, and then dried under reduced pressure, to give 12.14 g (34.7 mmol) of white crystals of 2-amino-6-chloro-9-(3,3-dicarbomethoxy-2,2-dichlorocyclopropyl)purine. The yield was 83.4%.

Incidentally, the obtained 2-amino-6-chloro-9-(3,3-dicarbomethoxy-2,2-dichlorocyclopropyl)purine has the following properties:

(1) EI-MS: 393($M^+$).

(2) $^1$H-NMR (300 MHz, DMSO-$d_6$) δ(ppm): 3.72 (s, 3H), 3.89 (s, 3H), 4.95 (s, 1H), 6.90–7.10 (br, 2H), 8.16 (s, 1H).

(3) $^{13}$C-NMR (75 MHz, DMSO-$d_6$) δ(ppm): 163.2, 161.6, 160.1, 154.9, 149.9, 142.2, 122.4, 60.4, 54.0, 46.2.

Example I-2

In a 0.25-liter autoclave, 4.0 g (10.1 mmol) of 2-amino-6-chloro-9-(3,3-dicarbomethoxy-2,2-dichlorocyclopropyl)purine obtained in Example I-1 and 2.0 g of 5% palladium carbon were added to 75 ml of methanol, and the resulting mixture was reacted with stirring for five hours under the condition that hydrogen gas was pressurized at about 5 $kgf/cm^2$. The reaction mixture was filtered, and the filtrate was concentrated under reduced pressure. Thereafter, 10 ml of water and 75 ml of ethyl acetate were added to the concentrate, and the resulting mixture was stirred for 30 minutes. The mixture was allowed to stand, and the layer containing ethyl acetate was collected. The resulting compound in the layer was purified by column chromatography, to give 1.78 g (6.07 mmol) of white crystals of dimethyl 2-(2-(2-aminopurine-9-yl)ethyl)malonate. The yield was 60.0%.

Incidentally, the obtained dimethyl 2-(2-(2-aminopurine-9-yl)ethyl)malonate has the following properties:

Melting Point: 106.5° C.

(1) EI-MS: 293($M^+$).

(2) $^1$H-NMR (300 MHz, $CDCl_3$) δ(ppm): 2.45–2.52 (m, 2H), 3.41 (t, 1H), 3.73 (s, 6H), 4.19–4.23 (m, 2H), 5.20–5.30 (br, 2H), 7.76 (s, 1H), 8.69 (s, 1H).

(3) $^{13}$C-NMR (300 MHz, $CDCl_3$) δ(ppm): 168.9, 160.1, 153.3, 149.9, 142.5, 128.1, 52.9, 48.8, 40.9, 28.7.

Example I-3

In a one-liter four-necked flask, 50.0 g (294.9 mmol) of 2-amino-6-chloropurine (manufactured by Sumika Fine Chemicals Co., Ltd.) and 88.2 g (648.0 mmol) of potassium carbonate were added to 650 ml of dimethylsulfoxide, and 26.1 g (1449.9 mmol) of water was then added to the resulting mixture. The resulting mixture was stirred at room temperature. Next, 127.4 g (440.0 mmol) of diethyl 2,2,2-trichloroethylidenemalonate, which was prepared by the process described in U.S. Pat. No. 3,495,012, was added to the resulting mixture, and the mixture was stirred for two hours and a half at room temperature. Thereafter, the reaction mixture was filtered, and the filtrate was poured into water. The precipitated crystals were collected by filtration, washed with 100 ml of water, and then dried under reduced pressure, to give 101.5 g (240.1 mmol) of white crystals of 2-amino-6-chloro-9-(3,3-dicarboethoxy-2,2-dichlorocyclopropyl)purine. The yield was 82.8%.

Incidentally, the obtained 2-amino-6-chloro-9-(3,3-dicarboethoxy-2,2-dichlorocyclopropyl)purine has the following properties:

(1) $^1$H-NMR (400 MHz, $CDCl_3$) δ(ppm): 1.25 (t, 3H), 1.39 (t, 3H), 4.24 (m, 2H), 4.41 (m, 2H), 4.76 (s, 1H), 5.29 (s, 1H), 8.03 (s, 1H).

(2) $^{13}$C-NMR (100 MHz, $CDCl_3$) δ(ppm): 162.5, 161.0, 159.2, 154.8, 151.6, 140.7, 124.2, 63.9, 63.3, 60.1, 47.2, 46.6, 14.1, 13.8.

Example I-4

10.0 g (23.7 mmol) Of 2-amino-6-chloro-9-(3,3-dicarboethoxy-2,2-dichlorocyclopropyl)purine and 10.0 g of 10% palladium carbon (manufactured by Kawaken Fine Chemicals Co., Ltd., 50% wet product) were added to 100 ml of ethyl acetate, and 8.04 g (118.2 mmol) of sodium formate was subsequently added to the resulting mixture. The resulting mixture was reacted for 16 hours at a temperature of 55° to 61° C., and the reaction mixture was then filtered. 25 ml Of water was poured into the resulting filtrate. The reaction mixture was neutralized with hydrochloric acid to allow phase separation, and the organic layer was concentrated. The concentrate residue was dissolved in ethyl acetate, and n-heptane was added dropwise to the resulting solution. The precipitated crystals were collected by filtration, and dried under reduced pressure, to give 4.14 g (12.9 mmol) of white crystals of diethyl 2-(2-(2-aminopurin-9-yl)ethyl)malonate. The yield was 54.5%.

It was confirmed from the following properties that the obtained crystals are diethyl 2-(2-(2-aminopurin-9-yl)ethyl) malonate.

(1) $^1$H-NMR (400 MHz, $CDCl_3$) δ(ppm): 1.25 (t, 6H), 2.47 (q, 2H), 3.35 (t, 1H), 4.19 (m, 6H), 5.14 (s, 2H), 7.77 (s, 1H), 8.69 (s, 1H).

(2) $^{13}$C-NMR (100 MHz, $CDCl_3$) δ(ppm): 168.3, 159.6, 153.1, 149.5, 142.4, 128.1, 61.9, 49.1, 40.9, 28.6, 14.1.

Example I-5

In a 0.3-liter four-necked flask, 15.0 g (88.5 mmol) of 2-amino-6-chloropurine (manufactured by Sumika Fine Chemicals Co., Ltd.) and 26.9 g (194.6 mmol) of potassium carbonate were added to 195 ml of dimethylsulfoxide, and 8.0 g (442.5 mmol) of water was then added to the resulting mixture. The resulting mixture was stirred at room temperature. Next, 42.2 g (132.9 mmol) of diisopropyl 2,2,2-trichloroethylidenemalonate, which was prepared by the process described in U.S. Pat. No. 3,495,012, was added to the resulting mixture, and the mixture was stirred for two hours and a half at room temperature. Thereafter, the reaction mixture was filtered, and the filtrate was poured into water. The precipitated crystals were washed with 100 ml of water, collected by filtration, and then recrystallized from isopropyl alcohol, to give 27.1 g (60.1 mmol) of pale yellow crystals of 2-amino-6-chloro-9-(3,3-dicarboisopropoxy-2,2-dichlorocyclopropyl)purine. The yield was 67.9%.

Incidentally, the obtained 2-amino-6-chloro-9-(3,3-dicarboisopropoxy-2,2-dichlorocyclopropyl)purine has the following properties:

(1) $^1$H-NMR (400 MHz, CDCl$_3$) δ(ppm): 1.23 (d, 3H), 1.26 (d, 3H), 1.36 (d, 3H), 1.38 (d, 3H), 4.74 (s, 1H), 5.08 (m, 1H), 5.23 (m, 1H), 5.34 (s, 2H), 8.04 (s, 1H).

(2) $^{13}$C-NMR (100 MHz, CDCl$_3$) δ(ppm): 162.0, 160.4, 159.2, 154.9, 151.5, 140.7, 124.2, 72.3, 71.7, 60.1, 47.3, 46.4, 21.8, 21.6, 21.4.

Example I-6

5.0 g (11.1 mmol) Of 2-amino-6-chloro-9-(3,3-dicarboisopropoxy-2,2-dichlorocyclopropyl)purine and 5.0 g of 10% palladium carbon (manufactured by Kawaken Fine Chemicals Co., Ltd., 50% wet product) were added to 100 ml of isopropyl alcohol, and 3.8 g (55.5 mmol) of sodium formate was subsequently added to the resulting mixture. The resulting mixture was reacted for 16 hours at a temperature of 55° to 61° C., and the reaction mixture was then filtered. 25 ml Of water was poured into the filtrate. The reaction mixture was neutralized with hydrochloric acid to allow phase separation, and the organic layer was concentrated. The concentrate residue was dissolved in ethyl acetate, and n-heptane was added dropwise to the resulting solution. The precipitated crystals were collected by filtration, and dried under reduced pressure, to give 2.4 g (6.9 mmol) of white crystals of diisopropyl 2-(2-(2-aminopurin-9-yl)ethyl)malonate. The yield was 62.4%.

It was confirmed from the following properties that the obtained crystals are diisopropyl 2-(2-(2-aminopurin-9-yl) ethyl)malonate.

(1) $^1$H-NMR (400 MHz, CDCl$_3$) δ(ppm): 1.24 (d, 6H), 1.25 (d, 6H), 2.44 (q, 2H), 3.28 (t, 1H), 4.21 (t, 2H), 5.05 (m, 2H), 5.09 (s, 2H), 7.76 (s, 1H), 8.69 (s, 1H).

(2) $^{13}$C-NMR (100 MHz, CDCl$_3$) δ(ppm): 167.9, 159.7, 153.0, 149.7, 142.3, 128.2, 69.5, 49.4, 40.9, 28.5, 21.7, 21.6

Example I-7

In a 0.3-liter four-necked flask, 4.13 g (25.0 mmol) of 2-amino-6-methoxypurine (manufactured by Sumika Fine Chemicals Co., Ltd.) and 7.6 g (55.0 mmol) of potassium carbonate were added to 110 ml of N,N-dimethylformamide, and the resulting mixture was stirred at room temperature. Next, 9.8 g (37.5 mmol) of dimethyl 2,2,2-trichloroethylidenemalonate, which was prepared by the process described in U.S. Pat. No. 3,495,012, was added to the resulting mixture, and the mixture was stirred for two hours and a half at room temperature. Thereafter, the reaction mixture was filtered, and the filtrate was poured into water. The precipitated crystals were collected by filtration, washed with 165 ml of water, and then dried under reduced pressure, to give 8.81 g (22.6 mmol) of white crystals of 2-amino-9-(3,3-dicarbomethoxy-2,2-dichlorocyclopropyl)-6-methoxypurine. The yield was 90.3%.

Incidentally, the obtained 2-amino-9-(3,3-dicarbomethoxy-2,2-dichlorocyclopropyl)-6-methoxypurine has the following properties:

(1) $^1$H-NMR (400 MHz, DMSO-d$_6$) δ(ppm): 3.72 (s, 3H), 3.88 (s, 3H), 3.97 (s, 3H), 4.94 (s, 1H), 6.54 (s, 2H), 7.86 (s, 1H).

(2) $^{13}$C-NMR (100 MHz, DMSO-d$_6$) δ(ppm): 163.0, 161.2, 160.6, 159.8, 154.7, 138.0, 112.6, 60.3, 54.2, 53.8, 53.3, 46.1, 46.0.

Example I-8

In a 0.3-liter four-necked flask, 6.03 g (25.0 mmol) of 2-amino-6-benzyloxypurine (manufactured by Sumika Fine Chemicals Co., Ltd.) and 7.6 g (55.0 mmol) of potassium carbonate were added to 160 ml of N,N-dimethylformamide, and the resulting mixture was stirred at room temperature. Next, 9.8 g (37.5 mmol) of dimethyl 2,2,2-trichloroethylidenemalonate, which was prepared by the process described in U.S. Pat. No. 3,495,012, was added to the resulting mixture, and the mixture was stirred for two hours and a half at room temperature. Thereafter, the reaction mixture was filtered, and the filtrate was poured into water. The precipitated crystals were collected by filtration, washed with 240 ml of water, and then dried under reduced pressure, to give 11.0 g (23.6 mmol) of white crystals of 2-amino-6-benzyloxy-9-(3,3-dicarbomethoxy-2,2-dichlorocyclopropyl)purine. The yield was 94.5%.

Incidentally, the obtained 2-amino-6-benzyloxy-9-(3,3-dicarbomethoxy-2,2-dichlorocyclopropyl)purine has the following properties:

(1) $^1$H-NMR (400 MHz, DMSO-d$_6$) δ(ppm): 3.72 (t, 3H), 3.88 (t, 3H), 4.94 (s, 1H), 5.50 (dd, 2H), 6.59 (s, 2H), 7.35–7.52 (m, 5H), 7.87 (s, 1H).

(2) $^{13}$C-NMR (100 MHz, DMSO-d$_6$) δ(ppm): 163.0, 161.2, 160.0, 159.7, 154.9, 138.2, 136.4, 128.4, 128.3, 128.0, 112.6, 67.0, 60.3, 54.2, 53.9, 46.1, 46.0.

Example I-9

5.0 g (12.6 mmol) Of 2-amino-6-chloro-9-(3,3-dicarbomethoxy-2,2-dichlorocyclopropyl)purine and 5.0 g of 5% palladium carbon were added to 75 ml of methanol, and the resulting mixture was then reacted for five hours at a temperature of 90° C. under the condition that hydrogen gas was pressurized at about 5 kgf/cm$^2$. The reaction mixture was filtered, and the filtrate was concentrated under reduced pressure. 10 ml Of water and 75 ml of ethyl acetate were added to the resulting residue. The resulting mixture was stirred for thirty minutes, and the layer containing ethyl acetate was then collected. The resulting product was purified by column chromatography, to give 1.8 g (6.3 mmol) of white crystals of dimethyl 2-(2-(2-aminopurin-9-yl) ethylmalonate. The yield was 50.0%. The resulting crystals were analyzed by high-performance liquid chromatography, and the purity was found to be 98.8%.

It is clear from the above results that the purine derivatives having a cyclopropane ring can be easily prepared by processes in Examples I-1, I-3, I-5, and I-7 to I-9. In addition, it is clear that the desired cyclopropane ring-cleaved purine derivative, which are useful for preparation intermediates of the preparation for antiviral agents, can be efficiently obtained in high yields from the purine derivatives having a cyclopropane ring by the processes in Examples I-2, I-4, and I-6.

Example II-1

10.0 g (25.3 mmol) Of 2-amino-6-chloro-9-(3,3-dicarbomethoxy-2,2-dichlorocyclopropyl)purine was dissolved in 300 ml of N,N-dimethylformamide. Subsequently, 2.9 g (76.7 mmol) of sodium borohydride was added to the resulting solution, and the resulting reaction solution was heated to 30° C. While keeping the same temperature, 30 ml of methanol was added dropwise to the reaction solution with stirring over one hour, and heated and stirred for additional one hour at a temperature of 30° to 40° C.

After the termination of reaction, the reaction solution was cooled to 10° C., and 80 ml of water was added to the reaction solution. 6 g Of acetic acid was added dropwise to the reaction solution, to adjust the pH of the reaction solution to 6.5, and a half of the amount of the solvent was then distilled off under reduced pressure. The precipitated crystals were collected by filtration, and washed with 10 ml of water twice. The obtained white crystals were dried under reduced pressure, to give 5.58 g (16.4 mmol) of 2-amino-6-chloro-9-[2,2-dichloro-3,3-bis(hydroxymethyl)cyclopropyl]purine. The yield was 65%.

It was confirmed from the following properties that the obtained white crystals are 2-amino-6-chloro-9-[2,2-dichloro-3,3-bis(hydroxymethyl)cyclopropyl]purine.

(1) $^1$H-NMR (270 MHz, DMSO-$d_6$): δ(ppm): 8.07 (s, 1H), 6.6–7.4 (brs, 2H), 4.06 (d, 1H, J=11.6 Hz), 3.96 (s, 1H), 3.92 (d, 1H, J=11.6 Hz), 3.65 (t, 2H, J =12.5 Hz).

(2) $^{13}$C-NMR (67.5 MHz, DMSO-$d_6$): δ(ppm): 160.1, 155.3, 159.7, 142.3,. 122.8, 65.1, 60.9, 57.4, 43.9, 41.1.

Example II-2

5.0 g (12.7 mmol) Of 2-amino-6-chloro-9-(3,3-dicarbomethoxy-2,2-dichlorocyclopropyl)purine was suspended in 100 ml of 1,3-dimethyl-2-imidazolidinone, and 1.9 g (88.6 mmol) of lithium borohydride was added to the resulting mixture. Subsequently, 20 ml of methanol was added dropwise to the mixture over one hour at a temperature of 5° to 10° C. After the termination of dropwise addition, the resulting reaction solution was stirred for additional two hours.

After the termination of reaction, 2 M hydrochloric acid was added to the reaction solution to adjust the pH of the reaction solution to 6.8, and the solvent was then distilled off under reduced pressure. 30 ml Of water was added to the resulting residue, the resulting mixture was then extracted with 60 ml of ethyl acetate three times. The resulting organic layers were combined, and the solvent was distilled off under reduced pressure. 30 ml Of water was added to the resulting residue to precipitated crystals. The crystals were collected by filtration. The obtained white crystals were dried under reduced pressure, to give 3.0 g (8.86 mmol) of 2-amino-6-chloro-9-[2,2-dichloro-3,3-bis(hydroxymethyl)cyclopropyl]purine. The yield was 70%.

It was confirmed that the obtained crystals are 2-amino-6-chloro-9-[2,2-dichloro-3,3-bis(hydroxymethyl)cyclopropyl]purine by the similar process to that in Examples II-1.

Example II-3

3.0 g (8.9 mmol) Of 2-amino-6-chloro-9-[2,2-dichloro-3,3-bis(hydroxymethyl)cyclopropyl]purine was suspended in 100 ml of ethyl acetate. Subsequently, 2.1 g (27 mmol) of pyridine and 0.1 g (0.9 mmol) of 4-dimethylaminopyridine were added to the resulting mixture, and the resulting reaction mixture was heated to 30° C. While keeping the same temperature, 2.2 g (21 mmol) of acetic anhydride was added dropwise to the reaction mixture with stirring, and heated and stirred for additional one hour at a temperature of 30° to 40° C.

After the termination of reaction, the reaction solution was cooled to 10° C., and 50 ml of water was added to the reaction solution to allow phase separation. The aqueous layer was extracted with 50 ml of ethyl acetate three times. The resulting organic layers were combined, washed with 50 ml of 5% sodium hydrogencarbonate twice, washed 50 ml saturated brine once, and then dried over 3.0 g of anhydrous magnesium sulfate. The resulting solid was filtered, the resulting filtrate was concentrated, and the precipitated crystals were collected by filtration. The obtained white crystals were dried under reduced pressure, to give 3.0 g (7.1 mmol) of 2-amino-6-chloro-9-(3,3-bis(acetoxymethyl)-2,2-dichlorocyclopropyl)purine. The yield was 80%.

It was confirmed from the following properties that the obtained white crystals are 2-amino-6-chloro-9-(3,3-bis(acetoxymethyl)-2,2-dichlorocyclopropyl)purine.

(1) $^1$H-NMR (270 MHz, CDCl$_3$): δ(ppm): 7.91 (s, 1H), 5.20–5.40 (brs, 2H), 4.72 (d, 1H, J =12.2 Hz), 4.60 (d, 1H, J=12.2 Hz), 4.45 (d, 1H, J=12.2 Hz), 4.01 (d, 1H, J=12.2 Hz), 3.91 (s, 1H), 2.20 (s, 3H), 2.13 (s, 3H).

(2) $^{13}$C-NMR (67.5 MHz, CDCl$_3$): δ(ppm): 170.5, 170.1, 159.4, 154.5, 151.9, 141.5, 124.6, 63.2, 63.0, 61.1, 45.4, 37.9, 20.8, 20.6.

Example II-4

2.8 g (8.2 mmol) Of 2-amino-6-chloro-9-[2,2-dichloro-3,3-bis(hydroxymethyl)cyclopropyl]purine obtained in Example II-1 and 2.0 g of 5% palladium carbon were added to 75 ml of methanol, and the resulting mixture was reacted for five hours at a temperature of 90° C. under the condition that hydrogen gas was pressurized at about 5 kgf/cm$^2$. The reaction mixture was filtered, and the filtrate was concentrated under reduced pressure, to give a white solid. Thereafter, the white solid was purified by column chromatography, to give 1.4 g (6.2 mmol) of white crystals of 2-amino-9-(4-hydroxy-3-hydroxymethylbutyl)purine. The yield was 75%, and the purity was 98%.

It was confirmed from the following properties that the obtained white crystals are 2-amino-9-(4-hydroxy-3-hydroxymethylbutyl)purine.

(1) Melting Point: 154–155° C. (lit. value: 153–155° C.)

Example II-5

2.8 g (6.6 mmol) of 2-amino-6-chloro-9-(3,3-bis(acetoxymethyl)-2,2-dichlorocyclopropyl)purine obtained in Example II-3 and 2.0 g of 5% palladium carbon were added to 75 ml of ethyl acetate, and the resulting mixture was reacted for five hours at a temperature of 90° C. under the condition that hydrogen gas was pressurized at about 5 kgf/cm$^2$. The reaction mixture was filtered, and the filtrate was concentrated under reduced pressure, to give a white solid. Thereafter, the white solid was recrystallized from 1-butanol, to give 1.7 g (5.3 mmol) of white crystals of 2-amino-9-(4-acetoxy-3-acetoxymethylbutyl)purine. The yield was 60%, and the purity was 97%.

It was confirmed from the following properties that the obtained crystals are 2-amino-9-(4-acetoxy-3-acetoxymethylbutyl)purine.

(1) Melting Point: 102–103° C. (lit. value: 102–103° C.)

Example II-6

2.8 g (8.2 mmol) of 2-amino-6-chloro-9-[2,2-dichloro-3,3-bis(hydroxymethyl)cyclopropyl]purine obtained in Example II-1 and 2.0 g of 5% palladium carbon were added to 75 ml of methanol, and 2.8 g (41 mmol) of sodium formate were added dropwise to resulting mixture over thirty minutes at a temperature of 60° C. The resulting mixture was stirred for seven hours at a temperature of 60° C. The reaction mixture was filtered, and the filtrate was concentrated under reduced pressure, to give a white solid. Thereafter, the white solid was purified with an ion-exchange resin, to give 1.6 g (7.1 mmol) of white crystals of 2-amino-9-(4-hydroxy-3-hydroxymethylbutyl)purine. The yield was 86%, and the purity was 98%.

It was confirmed that the obtained crystals are 2-amino-9-(4-hydroxy-3-hydroxymethylbutyl)purine by the similar process to that in Example II-4.

According to the processes in Examples II-1 to II-6, it is found from the above results that the purine derivatives having a cyclopropane ring can be easily obtained, and the cyclopropane ring-cleaved purine derivatives, which are useful for preparation intermediates for antiviral agents, can be easily obtained in high yields and at high purity by using the purine derivatives having a cyclopropane ring.

Example III-1

139.0 g (352.2 mmol) Of 2-amino-6-chloro-9-(3,3-dicarbomethoxy-2,2-dichlorocyclopropyl)purine and 139.0 g of 10% palladium carbon (manufactured by Kawaken Fine Chemicals Co., Ltd., 50% wet product) were added to 2780 ml of methanol, and 135.2 g (1988 mmol) of sodium formate was subsequently added to the resulting mixture. The resulting mixture was reacted for seven hours at a temperature of 55° to 61° C., and the reaction mixture was then filtered. The filtrate was concentrated under reduced pressure, and the resulting concentrate was suspended in 2400 ml of tetrahydrofuran. The insoluble inorganic salt was separated by filtration, and the filtrate was concentrated and dried, to give white crystals. Thereafter, the resulting white crystals were recrystallized from 210 ml of 2-propanol, to give 93.0 g (317.0 mmol) of white crystals of dimethyl 2-(2-(2-aminopurin-9-yl)ethyl)malonate. The yield was 90.0%. The resulting crystals were analyzed by high-performance liquid chromatography, and the purity was found to be 99.0%.

It was confirmed from the following properties that the obtained crystals are dimethyl 2-(2-(2-aminopurin-9-yl)ethyl)malonate.

(1) Melting Point: 111°–112° C. (lit. value: 110°–112° C.)

(2) $^1$H-NMR (270 MHz, DMSO-$d_6$) δ(ppm): 8.54 (s, 1H), 7.98 (s, 1H), 6.45 (brs, 2H), 4.10 (t, 3H), 3.58 (s, 6H), 3.49 (t, 1H), 2.32 (q, 2H).

(3) $^{13}$C-NMR (67.5 MHz, DMSO-$d_6$) δ(ppm): 168.7, 160.4, 152.9, 148.9, 142.5, 126.8, 52.4, 48.4.

Example III-2

The same procedures as in Example III-1 were carried out except that 125.3 g (1988 mmol) of ammonium formate was used in place of sodium formate. Since the reaction stopped after two hours, additional 125.3 g (1988 mmol) of ammonium formate was added to the reaction mixture. Thereafter, since the reaction stopped again, additional 125.3 g (1988 mmol) of ammonium formate was added to the reaction mixture. The same operations of adding the same amount of ammonium formate after stopping the reaction were repeated, and the time required for termination of reaction was 16 hours from the start of reaction. As a consequence, 2506 g of ammonium formate was required by the completion of reaction.

The resulting product was 92.0 g (313.7 mmol) of white crystals of dimethyl 2-(2-(2-aminopurin-9-yl)ethyl) malonate having similar properties to the white crystals obtained in Example III-1. The yield was 89.0%. The resulting crystals were analyzed by high-performance liquid chromatography, and the purity was found to be 98.9%.

Example III-3

The same procedures as in Example III-1 were carried out except that 167.2 g (1988 mmol) of potassium formate was used in place of sodium formate, to give 90.9 g (309.9 mmol) of white crystals of dimethyl 2-(2-(2-aminopurin-9-yl)ethyl)malonate having similar properties to the white crystals obtained in Example III-1. The yield was 88.0%. The resulting crystals were analyzed by high-performance liquid chromatography, and the purity was found to be 99.0%.

Example III-4

The same procedures as in Example III-1 were carried out except that 102.6 g (352.2 mmol) of 2-amino-9-(3,3-dicarbomethoxycyclopropyl)purine was used in place of 2-amino-6-chloro-9-(2,2-dichloro-3,3-dicarbomethoxycyclopropyl)purine and that 24.8 g (528.4 mmol) of 98% formic acid was used in place of sodium formate, to give 90.5 g (308.6 mmol) of white crystals of dimethyl 2-(2-(2-aminopurin-9-yl)ethyl)malonate. The yield was 87.6%. The resulting crystals were analyzed by high-performance liquid chromatography, and the purity was found to be 99.0%.

According to the processes in Examples III-1 to III-4, it is found from the above results that the cyclopropane ring-cleaved compound can be obtained in high yields without taking the procedures of which safety is at risk in that the reaction system is pressurized with hydrogen gas as in the conventional process.

Example IV

In a 100 ml four-necked flask, 1.5 g (8.8 mmol) of 2-amino-6-chloropurine (manufactured by Sumika Fine Chemicals Co., Ltd.) and 2.0 g (19.8 mmol) of triethylamine were added to 38 ml of N,N-dimethylformamide, and the resulting mixture was stirred at room temperature. Next, 3.5 g (13.4 mmol) of dimethyl 2,2,2-trichloroethylidenemalonate, which was prepared by the process described in U.S. Pat. No. 3,495,012, was added to the resulting mixture, and the mixture was stirred for two hours at room temperature. To the reaction mixture, 30 ml of water was added, and the obtained mixture was extracted with 70 ml aliquots of ethyl acetate three times. The ethyl acetate layers were combined, and the combined mixture was washed with 50 ml of a saturated brine. Thereafter, the washed mixture was dehydrated by adding 10 g of anhydrous magnesium sulfate. After separating magnesium sulfate by filtration, the filtrate was concentrated under reduced pressure. The resulting concentrate was crystallized from ethyl acetate-heptane mixture. The precipitated crystals were collected by filtration, and dried under reduced pressure, to give 2.05 g (22.6 mmol) of white crystals of dimethyl 1-(2-amino-6-chloropurin-9-yl)-2,2,2-trichloroethylmalonate. The yield was 54.1%.

Incidentally, the obtained dimethyl 1-(2-amino-6-chloropurin-9-yl)-2,2,2-trichloroethylmalonate has the following properties:

(1) $^1$H-NMR (400 MHz, CDCl$_3$) δ(ppm): 3.54 (s, 3H), 3.85 (s, 3H), 4.62 (s, 1H), 5.67 (s, 2H), 6.31 (s, 1H), 8.10 (s, 1H).

(2) $^{13}$C-NMR (100 MHz, CDCl$_3$) δ(ppm): 165.6, 164.8, 159.5, 154.7, 151.7, 139.2, 123.4, 98.2, 77.2, 65.4, 53.9, 53.6.

According to the present invention, the purine derivative having a cyclopropane ring can be easily prepared. In addition, according to the present invention, a high-purity, cyclopropane ring-cleaved purine compound can be prepared readily, in a high yield, and efficiently from the purine derivative having a cyclopropane ring. Further, according to the present invention, an effect that a cyclopropane ring-cleaved compound can be prepared with good operability and safely and in a high yield can be well exhibited.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for preparing a cyclopropane ring-cleaved purine derivative represented by the formula (X):

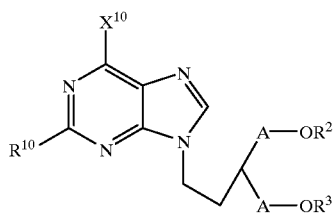

(X)

wherein A is a —CH$_2$— group or —CO— group; $X^{10}$ is a hydrogen atom, an alkoxy group having 1 to 10 carbon atoms, or hydroxyl group; and each of $R^2$ and $R^3$ is independently a hydrogen atom, an alkyl group having 1 to 7 carbon atoms, which may have a substituent, an aralkyl group having 7 to 11 carbon atoms, which may have a substituent, or an acyl group represented by the formula RC(O)— wherein R is a hydrogen atom or an alkyl group having 1 to 6 carbon atoms, which may have a substituent; and $R^{10}$ is a hydrogen atom or a protected or unprotected amino group, with proviso that in a case where A is a —CO— group, neither $R^2$ nor $R^3$ is an acyl group, said substituent being selected from the group consisting of an alkoxy group having 1 to 6 carbon atoms, a hydroxy group, a nitro group, an amino group, a halogen atom, and a cyano group, comprising hydrogenating a purine derivative having a cyclopropane ring represented by the formula (I):

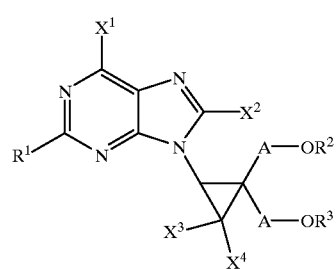

(I)

wherein $X^1$ is a hydrogen atom, a halogen atom, an alkoxy group having 1 to 10 carbon atoms, or hydroxyl group; each of $X^2$, $X^3$, and $X^4$ is independently a hydrogen atom or a halogen atom; $R^1$ is a hydrogen atom, a halogen atom, or a protected or unprotected amino group; and A, $R^2$ and $R^3$ the same as defined above, with proviso that in a case where A is a —CO— group, neither $R^2$ nor $R^3$ is an acyl group, said substituent being selected from the group consisting if an alkoxy group having 1 to 6 carbon atoms, a hydroxy group, a nitro group, an amino group, a halogen atom, and a cyano group.

* * * * *